United States Patent
Macleish et al.

(10) Patent No.: US 9,777,255 B2
(45) Date of Patent: Oct. 3, 2017

(54) METHODS AND STORAGE AND RETRIEVAL OF FUNCTIONAL MATURE RETINAL CELLS

(75) Inventors: Peter R. Macleish, Sandy Springs, GA (US); Xiaoming Chen, Atlanta, GA (US)

(73) Assignee: MOREHOUSE SCHOOL OF MEDICINE, Atlanta, GA (US)

(*) Notice: Subject to any disclaimer, the term of this patent is extended or adjusted under 35 U.S.C. 154(b) by 155 days.

(21) Appl. No.: 12/967,696

(22) Filed: Dec. 14, 2010

(65) Prior Publication Data

US 2012/0148536 A1    Jun. 14, 2012

(51) Int. Cl.
- *C12N 5/0793* (2010.01)
- *A01N 1/02* (2006.01)
- *A61K 35/30* (2015.01)

(52) U.S. Cl.
CPC .............. *C12N 5/062* (2013.01); *A01N 1/021* (2013.01); *A61K 35/30* (2013.01)

(58) Field of Classification Search
CPC ......... C12N 5/062; A01N 1/021; A61K 35/30
See application file for complete search history.

(56) References Cited

U.S. PATENT DOCUMENTS

| | | | |
|---|---|---|---|
| 2005/0059148 A1* | 3/2005 | Kubota | 435/368 |
| 2005/0059595 A1* | 3/2005 | Lasko et al. | 514/12 |
| 2010/0233136 A1* | 9/2010 | Aberdam et al. | 424/93.7 |

FOREIGN PATENT DOCUMENTS

WO    WO 9955838 A1 * 11/1999

OTHER PUBLICATIONS

Valtink et al, Physiological features of priamry cultures and subcultures of human retinal pigment epithelial cells before and after cryopreservation for cell transplantation, 1999, Graefe's Archive for clinical and Experimental Ophthamology, vol. 237, pp. 1001-1006.*
Papain, Sigma-Aldrich, http://www.sigmaaldrich.com/etc/medialib/docs/Sigma/Datasheet/5/p3125dat.Par.0001.File.tmp/p3125dat.pdf.*
Grozdanov et al , A Method for Preparing Primary Retinal Cell Cultures for Evaluating the Neoroprotective and Neuritogenic Effect of Factors on Axotomized Mature CNS Neurons, Current Protocols in Neuroscience, Oct. 1, 2010, Supplement 53, Subunit 3.22.1-3.22.10.*
ATCC, Formulation for Dulbecco's Modified Eagle's Medium (DMEM) ATCC® 30/2002, http://www.atcc.org/attachments/4890.pdf.*
Phenol Red (Phenol Red Dye, Abbey Color, http://www.abbeycolor.com/phenol-red.php.*
Biedermann et al., Patch-clamp recording of Muller glial cells after cryopreservation, 2002, Journal of Neuroscience Methods, vol. 120, pp. 173-178.*
Ugwu et al., The Effect of Buffers on Protein Conformational Stability, Pharmaceutical Technology, 2004, vol. 28, pp. 86-108.*
Lee et al., Differential expression and cellular localization of doublecortin in the developing rat retina, European Journal of Neuroscience, 2003, vol. 17, pp. 1542-1548.*
MEM-Sigma, Sigma, Formulation for Minimum Essential Medium Eagle (MEM), found at http://www.sigmaaldrich.com/life-science/cell-culture/learning-center/media-formulations/mem.html#mem.*
Balse et al., Purification of Mammalian Cone Photoreceptors by Lectin Panning and the Enhancement of Their Survival in Glia-Conditioned Medium, Investigative Ophthalmology and Visual Science, 2005, vol. 46, pp. 367-374.*
MEM II, Sigma-Aldrich, Formulation for Minimum Essential Medium Eagle (MEM), Accessed Jul. 1, 2015, http://www.sigmaaldrich.com/content/dam/sigma-aldrich/docs/Sigma/Formulation/m4655for.pdf.*
Geng Li et al., Rapid Regioselective Oligomerization of L-Glutamic Acid Diethyl Ester Catalyzed by Papain, Macromolecules, 2006, vol. 39, pp. 7915-7921.*
Uchihori, et al., Mifogenic and Chemotactic Effects of Platelet-Derived Growth Factor on Human Retinal Glial Cells, Investigative Ophthalmology & Visual Science, 1991, vol. 32, pp. 2689-2695.*
Lang et al., Modulation of the Inhibitory Substrate Properties of Oligodendrocytes by Platelet-Derived Growth Factor, Journal of Neuroscience, 1996, vol. 16, pp. 5741-5748.*

* cited by examiner

Primary Examiner — Robert Yamasaki
Assistant Examiner — Teresa E Knight
(74) Attorney, Agent, or Firm — Ping Wang; Andrews Kurth Kenyon LLP

(57) ABSTRACT

A method for the isolation, storage and retrieval of mature retinal cells is disclosed. The Method is applicable to adult mammalian cone cells, and more particularly human cone cells, and to healthy as well as pathological or otherwise altered cone cells. A kit for the isolation, storage and retrieval of mature retinal cells is also described.

18 Claims, 5 Drawing Sheets

METHODS AND STORAGE AND RETRIEVAL OF FUNCTIONAL MATURE RETINAL CELLS

FIELD

The present application relates generally to the field of cell isolation and storage and, in particular, to the isolation, storage and retrieval of functional mature retinal cells.

BACKGROUND

Nearly 10 million Americans are blind or suffer visual impairment due to glaucoma, retinitis pigmentosa, age-related macular degeneration and diabetic retinopathies. These diseases are all due to the loss of one or more retinal cell type and according to the most recent statistics represent 36% of the existing cases of legal blindness in the United States. Every year an additional 230,000 patients are diagnosed with these diseases. Current treatments can slow disease progression, but cannot replace lost retinal cells.

The isolation of retinal neurons from the adult retina provided an opportunity to perform electrophysiological experiments that is virtually impossible in the intact retina. Transplantation of retinal cells, especially adult retinal stem cells, have been used in the treatment for diseases involving the loss of retinal neurons, such as glaucoma, retinitis pigmentosa, and age macular degeneration. However, successful use of adult retinal cells for research and transplantation has been impeded by the difficulty in propagating and maintaining these cells. Following isolation, retinal cells remain viable for only a couple of days thereby limiting the use of the majority of cells that were obtained as a result of the retinal dissociation. Therefore, there still exists a need for new methods for of isolating, storing and retrieving functional mature retinal cells.

SUMMARY

One aspect of the present invention relates a method for the isolation and storage of mature retinal cells. The method includes incubating freshly isolated retinal tissue with a retinal tissue digestion solution containing a protease, removing the retinal tissue digestion solution, triturating enzyme-treated retinal tissue in a retinal cell suspension medium to form a retinal cell suspension, adding fetal bovine serum (FBS) and dimethyl sulfoxide (DMSO) to the retinal cell suspension, and storing the retinal cell suspension in liquid nitrogen.

In an embodiment, the retinal cells are selected from the group consisting of cone cells, rod bipolar cells, rod cells, ganglion cells, glial cell and mixtures thereof.

In another embodiment, the retinal tissue is retina or retinal pigmented epithelium.

In another embodiment, the method further comprises dissecting the isolated retinal tissue into small fragments.

In another embodiment, the protease is selected from the group consisting of trypsin, chymotrypsin, pepsin, papain, elastase A and mixtures thereof.

In one embodiment, the protease is papain.

In another embodiment, the tissue digestion solution further contains a collagenase.

In another embodiment, the tissue digestion solution further contains an enzyme activator.

In one embodiment, the enzyme activator is cysteine.

In another embodiment, the tissue digestion solution comprises NaCl, $NaHCO_3$, sodium pyruvate, KCl, $NaH_2PO_4$ and $CaCl_2$.

In one embodiment, the tissue digestion solution comprises 114 mM NaCl, 25 mM $NaHCO_3$, 1 mM sodium pyruvate, 3 mM KCl, 0.5 mM $NaH_2PO_4$, 0.5 mM $CaCl_2$, and 0.02 mM Phenol red.

In another embodiment, the tissue digestion solution has a pH of 7.2-7.3.

In another embodiment, the freshly isolated retinal tissue is incubated with a retinal tissue digestion solution containing a protease at a temperature between about 18° C. and 42° C. for about 15-90 min.

In another embodiment, the freshly isolated retinal tissue is incubated with a retinal tissue digestion solution containing a protease at room temperature for about 30-40 min.

In another embodiment, the method further comprises thawing stored retinal cells; and mixing thawed cells with a retinal cell culture medium.

In a related embodiment, the retinal cell culture medium comprises a growth factor selected from the group consisting of human epidermal growth factor, human fibroblast growth factor-2 and platelet-derived growth factor.

Another aspect of the present invention relates to a method for treating retinal dysfunction in a subject. The method includes introducing into an eye of the subject an effective amount of retinal cells stored and retrieved using the method of the present invention.

In one embodiment, the retinal dysfunction is selected from the group consisting of photoreceptor degeneration, retinal detachment, retinal trauma, photic lesions caused by laser or sunlight; a macular hole, macular edema; night blindness and color blindness, ischemic retinopathy, and inflammatory conditions.

In another embodiment, the retinal cells are introduced into said eye with a substance that stimulate differentiation of neuroretina-derived stem cells into photoreceptor cells.

Another aspect of the present invention relates to a kit for isolating, storing and retrieving retinal cells. The kit includes a retinal cell digestion solution; a retinal cell suspension medium; a retinal cell culture medium, and instructions on how to isolate, store and retrieve retinal cells.

DETAILED DESCRIPTION

The practice of the embodiments described in further detail below will employ, unless other wise indicated, conventional methods cell biology, molecular biology, biochemistry, immunology and ophthalmology within the skill of the art. Such techniques are explained fully in the literature. All publications, patents and patent applications cited herein, whether supra or infra, are hereby incorporated by reference in their entirety.

Method for Harvesting, Storing and Retrieving Retinal Cells

Figure 1:
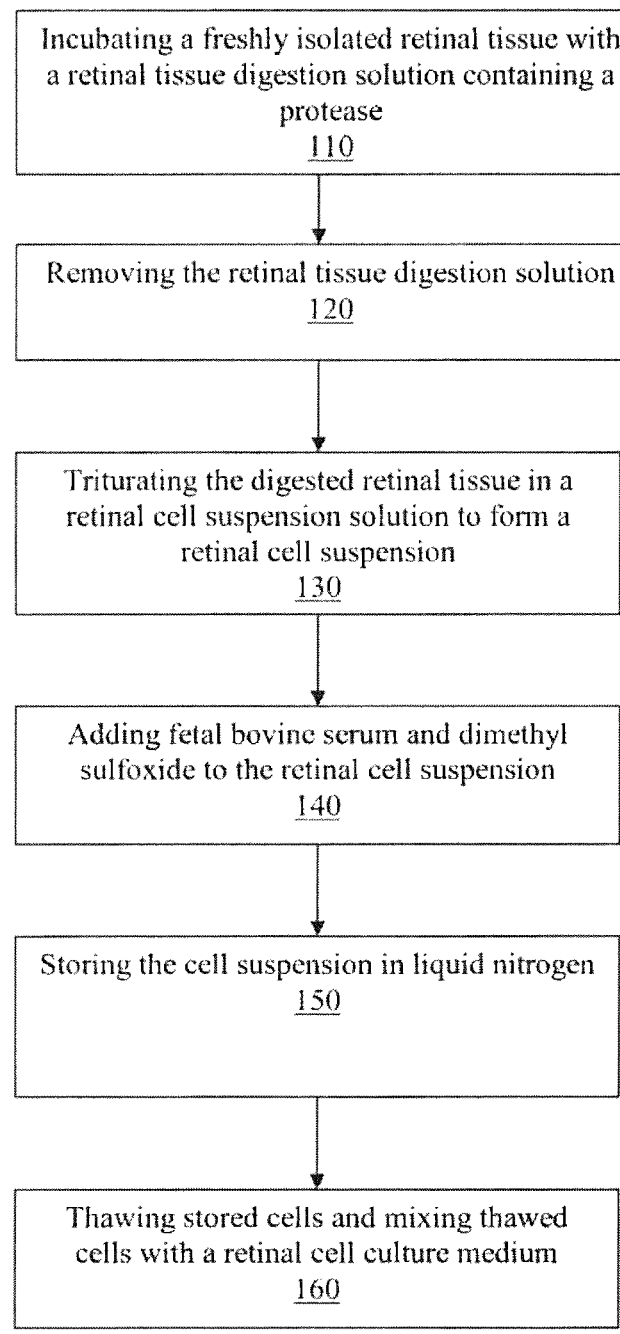
FIG. 1 is a flow chart showing a method for isolating, storing and retrieving retina cells.

One aspect of the present invention relates to a method for the isolation, storage and retrieval of mature retinal cells. The method 100 (FIG. 1) comprises the steps of incubating (110) a freshly isolated retinal tissue with a retinal tissue digestion solution containing a protease, removing (120) the retinal tissue digestion solution, triturating (130) the digested retinal tissue in a retinal cell suspension solution to form a retinal cell suspension, adding (140) fetal bovine serum (FBS) and dimethyl sulfoxide (DMSO) to the retinal cell suspension, storing (150) the cell suspension in liquid nitrogen, and thawing (160) stored cells and mixing thawed cells with a retinal cell culture medium.

Retinal Tissue

The term "retinal tissue" includes the retina or retinal pigmented epithelium. The retinal tissue can be a mammalian retinal tissue (primate or non-primate retinal tissue), e.g. a human retinal tissue, or an animal but non-human retinal tissue such as pig, rat, mouse retinal tissue. The retinal tissue can be a healthy tissue or a pathologic tissue, e.g. a retinal tissue undergoes or has undergone photoreceptor degeneration (cone and/or rod dysfunction). Isolation and storage of diseased retinal cells allows for screening for compounds capable of showing a protective and/or anti-disease effect on retinal cells, as well as genomics and proteomics applications, e.g., identifying genes and proteins that are specific or characteristic of the diseased retinal cells compared to healthy retinal cells (and vice versa).

The pathologic retinal tissue can originate from an individual afflicted with an inherited or acquired disease involving photoreceptor degeneration, such as retinitis piginentosa and age macular degeneration, or other maculopathies. The freshly isolated retinal tissue may optionally be dissected into small fragments (e.g., 1-2 mm by 1-2 mm, 2-3 mm by 2-3 mm or 3-5 mm by 3-5 mm), preferably under conditions non deleterious to retinal cell biology, i.e. under conditions that do not substantially impair the growth potential of the retinal cells, for example, in cold $CO_2$-independent medium.

Retinal Cell Digestion Solution

The retinal cell digestion solution contains one or more a proteolytie enzymes. Examples of the proteolytic enzymes include, but are not limited to, trypsin, chymotrypsin, pepsin, papain, elastase A and mixtures thereof. skilled person can adjust the dissociation conditions, such as temperature, enzyme concentration, and dissociation duration, as a function of the enzyme(s) used and of the retinal tissue to which it is applied. Illustrative conditions are mentioned in the Example below. The skilled person may also use an enzyme activator, such as cysteine, if desired. In certain embodiments, the retinal cell digestion solution further contains a collogenase.

The retinal cell digestion solution also contains a buffer and/or at least one salt or a combination of salts. In some embodiments, the pH of the retinal cell digestion solution ranges from about 5 to about 8, from about 6 to 8, or from about 7 to about 7.5. A variety of pH buffers may be used to achieve the desired pH. Suitable buffers include, but are not limited to, Tris, MES, Bis-Tris, ADA, ACES, PIPES, MOPSO, Bis-Tris propane, BES, MOPS, TES, HEPES, DIPSO, MOBS, TAPSO, HEPPSO, POPSO, TEA, HEPPS, Tricine, Gly-Gly, Bicine, and a phosphate buffer (e.g., sodium phosphate or sodium-potassium phosphate, among others). The retinal cell digestion solution may comprise from about 10 mM to about 100 mM buffer, about 25 mM to about 75 mM buffer, or from about 40 mM to about 60 mM buffer, among others. The type and amount of the buffer used in the retinal cell digestion solution can vary from application to application. In some embodiments, the retinal cell digestion solution has a pH of about 7.4, which can be achieved using about 50 mM Tris buffer. In another embodiment, the retinal cell digestion solution has a pH of about 7.2-7.3.

In one embodiment, the retinal cell digestion solution contains NaCl, $NaHCO_3$, sodium pyruvate, KCl, $NaH_2PO_4$ and $CaCl_2$. In another embodiment, the retinal cell digestion solution contains: 114 mM NaCl, 25 mM $NaHCO_3$, 1 mM sodium pyruvate, 3 mM KCl, 0.5 mM $NaH_2PO_4$, 0.5 mM $CaCl_2$, and 0.02 mM Phenol red. In another embodiment, the retinal cell digestion solution is prepared by adding 3 mg cysteine HCl, 20 mg glucose, 10-14 units/ml papain into 7 ml salt solution, bubbling solution with 5% CO2 and 95% $O_2$ for 10 min to reach pH 7.2-7.3.

Digestion Conditions

The freshly isolated tissue is treated with the retinal cell digestion solution to enzymatically digest the extracellular matrix of the retinal tissue or retinal tissue fragments, under conditions to dissociate the retinal cells from each other without substantially altering their cellular integrity, i.e. without lysing the retinal cells.

In certain embodiments, the freshly isolated retinal tissue is incubated at a temperature between 18° C. and 42° C. for a period of 15-90 minutes. In one embodiment, the freshly isolated retinal tissue is incubated in the retinal tissue digestion solution at room temperature for 30-40 minutes. After digestion, the retinal tissue digestion solution may be removed by aspiration. The digested retinal tissue is washed once or twice with the retinal cell storage medium and is triturated in 10-100 volumes of the retinal cell storage medium (i.e., if the original retinal tissue has a volume of 0.1 $cm^3$, the digested retinal tissue will be suspended in 1-10 ml of the retinal cell storage medium) to form a retinal cell suspension. The cell population obtained by the present invention typically comprises cone cells, rod bipolar cells, rod cells, ganglion cells and filial cells.

Retinal Cell Suspension Medium and Retinal Cell Storage Medium

The retinal cell suspension medium is selected as being suitable for retinal cell storage and survival. Suitable medium include, but are not limited to, DMEM/F12 medium (available e.g. from Invitrogen), RPM11640 (available e.g. from Invitrogen), Ames (available e.g. from Sigma), NBA™ (Neurobasal Medium, available from Invitrogen) and X-VIVO 15 serum-free medium.

The retinal cell storage medium is retinal cell suspension medium with 10% serum and 10% DMSO.

In one embodiment, the retinal cell suspension medium comprises 139 mM NaCl, 2 mM HEPES, 1 mM sodium pyruvate, 0.5 mM $MgCl_2$, 0.5 mM $MgSO_4$, 0.5 mM $NaH_2PO_4$, 1.8 mM $CaCl_2$, 3 mM KCl, 1 mM $NaHCO_3$, 0.1 mM Choline Cl, 0.02 mM Phenol red, 15 mM glucose, with 1 N NaOH added to adjust to pH 7.2-7.3. The retinal cell storage medium is prepared by adding 10% fetal bovine serum (FBS) and 10% DMSO to the above-described retinal cell suspension medium.

Storage Conditions

The retinal cell suspension is stored in the presence of fetal bovine serum (FBS) and dimethyl sulfoxide (DMSO). In certain embodiments, the retinal cells are suspended in the retinal cell suspension medium. FBS and DMSO are then added to the cell suspension to a final concentration of 5-20% (v/v) each, preferably 10% (v/v) each (e.g., 10 ml FBS and 10 ml DMSO for 80 ml cell suspension). In other embodiments, the retinal cells are suspended directly in the retinal cell storage medium.

The cell suspension is then aliquoted and stored in liquid nitrogen. In one embodiment, the aliquots are stored at −80° C. overnight and then transferred to liquid nitrogen. In another embodiment, the aliquots are snap-frozen in dry ice, stored at −80° C. overnight, and then transferred to liquid nitrogen. In yet another embodiment, the aliquots are snap-frozen in dry ice and then transferred to liquid nitrogen.

Retrieval Conditions

To preserve viability, the frozen retinal cells are thawed quickly in a water bath at 37° C. The thawed cells are washed with a warm retinal cell culture medium to remove DMSO and cultured in an incubator with 5% $CO_2$ at 37° C. In one embodiment, the thawed cells are mixed gently with 10-20 fold volume of the retinal cell culture medium and centrifuged at 100×g for 3 min. The supernatant is discarded. The pellet is resuspended in the retinal cell culture medium.

Retinal Cell Culture Medium

In one embodiment, the retinal cell storage medium contains a serum-free culture medium; at least one growth factor at a final concentration of about 0.1 ng/mL to about 40 ng/mL, preferably 10 ng/mL to about 30 ng/mL, at least one neural supplement at a final concentration of about 0.1% v/v to about 10% v/v, preferably about 0.5% v/v to about 3% v/v of the retinal cell storage medium, and optionally a heat-inactivated serum comprising from about 0.1% v/v to about 20% v/v, preferably from about 5% v/v to about 15% v/v of the retinal cell storage medium.

As used herein, the term "% v/v" refers percentage by volume. For example, 1% v/v is equivalent to 1 part volume per every 100 part volume of the retinal cell culture medium.

In one embodiment, the retina cell culture medium contains NaCl, HEPES, sodium pyruvate, $MgCl_2$, $MgSO_4$, $NaH_2PO_4$, $CaCl_2$, KCl, $NaHCO_3$, and Choline Cl, In another embodiment, the retina cell culture medium contains 139 mM NaCl, 2 mM HEPES, 1 mM sodium pyruvate, 0.5 mM $MgCl_2$, 0.5 mM $MgSO_4$, 0.5 mM $NaH_2PO_4$, 1.8 mM $CaCl_2$, 3 mM KCl, 1 mM $NaHCO_3$, 0.1 mM Choline Cl, 0.02 mM Phenol red, and 15 mM glucose, adjusted to pH 7.2-7.3 with 1 N NaOH. In another embodiment, the retina cell culture medium further contains 0.01% BSA for short term culture.

The retinal cell culture medium may further contain a growth factor, a neural supplement, glutamine and/or serum.

In some embodiments, the growth factor is recombinant human epidermal growth factor (hrEGF), recombinant human fibroblast growth factor-2 (hrFGF-2), or platelet-derived growth factor (PDGF). Recombinant human, fibroblast growth factor-2 (hrFGF-2) is also known as basic fibroblast growth factor (bFGF). In some embodiments, the first growth factor is recombinant human basic fibroblast growth factor-2 (hrbFGF-2).

In some embodiments, the neural supplement is N-2 supplement (Gibco, Invitrogen) or B-27 supplement (Gibco, Invitrogen). N-2 supplement contains 500 μg/ml insulin, 10 mg/ml h-transferrin, 0.63 μg/ml progesterone, 1.611 mg/ml putrascine, and 0.52 μg/ml selenite.

In some other embodiments, the neural supplement comprises insulin at about 100 μg/ml to about 1000 pg/ml of the culture medium; h-transferrin at about 0.1 mg/ml to about 100 mg/ml of the culture medium; progesterone at about 0.1 pg/ml to about 10 μg/ml of the culture medium; putrascine at about 0.1 mg/ml to about 10 mg/ml of the culture medium; and selenite at about 0.01 μg/ml to about 10 μg/ml of the culture medium.

In some other embodiments, the neural supplement comprises insulin at about 300 μg/ml to about 700 μg/ml of the culture medium; h-transferrin at about 5 mg/ml to about 15 mg/ml of the culture medium; progesterone at about 0.3 μg/ml to about 0.9 μg/ml of the culture medium; putrascine at about 1 mg/ml to about 2 mg/ml of the culture medium; and selenite at about 0.2 μg/ml to about 1 μg/ml of the culture medium.

In certain embodiments, the retinal cell culture medium is a preconditioned culture medium that is adapted to the in vitro culture of cone photoreceptor cells. Briefly, the culture medium is pre-conditioned by culturing Muller glial cells in a culture medium that is suitable for cone survival, and collecting the resulting culture medium. In one embodiment, the pre-conditioned culture medium is prepared by culturing Muller glial cells in NBA™ culture medium, optionally supplemented by B27 and glutamine, or DMEM/F12 medium, or Ames medium. The conditioned medium is typically collected at day 1 or 2 of the Muller glial cell culture on pre-conditioned medium.

Method for Treating Retinal Dysfunction

Another aspect of the present invention provides a method for treating retinal dysfunction in a mammal. The stored retinal cells can be used to treat a mammalian recipient suffering from a lack or diminution of photoreceptor cell function. Examples of retinal dysfunction that can be treated by the stored retinal cells include, but are not limited to: photoreceptor degeneration (as occurs in, e.g., hereditary or acquired retinitis pigmentosa, cone dystrophies, cone-rod and/or rod-cone dystrophies, and macular degeneration, including age-related and early onset macular degeneration); retinal detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as, e.g., CMV (cytomegalovirus) retinitis, herpes type 1 retinitis, Ebstein-Barr virus retinitis, toxoplasmosis, rubella and pox virus; inflammatory conditions, such as the uveitidies, multifocal choroiditis and uveitis, birdshot chorioretinopathy, collagen vascular diseases affecting the posterior segment of the eye, including Wegener's granulomatosis, uveitis associated with systemic lupus erythematosus, uveitis associated with polyarteritis nodosa, peripheral or intermediate uveitis, chronic central serous chorioretinopathy, and myopic choroidal neovascular membranes and scars. Inflammatory disorders also include Behcet syndrome, intermediate uveitis (pars planitis), masquerade syndromes, peripheral uveitis, ocular syphilis, ocular tuberculosis, viral-related chorioretinitis (ARN) syndrome, HIV-related uveitis, progressive outer retinal necrosis syndrome, sympathetic ophthalmia, white dot syndromes, presumed ocular histoplasmosis syndrome, acute macular neuroretinopathy, diffuse unilateral subacute neuroretinitis, ophthalmomyiasis, serpiginous choroidopathy, panuveitis, birdshot retinochoroidopathy, and uveitis associated with disorders such as juvenile rheumatoid arthritis, Kawasaki syndrome, multiple sclerosis, sarcoidosis, toxocariasis, toxoplasmosis, Vogt-Koyanagi-Harada (VKH), and HLA-B27 seropositive spondylopathy syndromes.

Other disorders include tumors, such as retinoblastoma and ocular melanoma. Additionally, stored retinal cells can be used for replacement of inner retinal neurons, which are affected in ocular neuropathies including glaucoma, traumatic optic neuropathy, degenerative optic neuropathy, ischemic optic neuropathy, optic neuropathy from multiple sclerosis, and radiation optic neuropathy and retinopathy.

The methods can also be used to treat optic nerve diseases such as optic atrophy, ischemic optic neuropathy, diabetes induced optic atrophy, optic nerve hypoplasia, morning glory syndrome, Graves ophthalmopathy, optic neuritis, cytomegalovirus neuritis, arteritic optic neuropathy, compressive neuropathy, diabetic neuropathy, giant cell arteritis, infiltrative neuropathy, nutriotional, ischemic neuropathy, retrobulbar optic neuritis, retrobulbar ischemic neuropathy, toxic neuropathy, traumatic neuropathy; optic nerve diseases resulting from causes such as syphilis, Lyme disease, toxoplasmosis, cat scratch disease, systemic lupus erythematosus, paraneoplastic syndrome, multiple sclerosis, and autoimmune disease; degenerative optic diseases such as age-related macular degeneration, early onset macular degeneration, Usher Syndrome, retinitis pigmentosa, cone-road dystrophy, and choroideremia; and congenital optical diseases such as Leber's congenital amaurosis, congenital stationary night blindness, and optic nerve hypoplasia. One of skill in the art will recognize that there is overlap between the various classifications of the disorders and conditions listed herein.

In some embodiments, the retinal dysfunction is a result of photoreceptor degeneration, retinal detachment, retinal trauma, a photic lesion, a macular hole, a macular edema, night blindness, color blindness, ischemic retinopathy, retinopathy due to premature birth, infection, inflammatory condition, or an ocular neuropathy. In some embodiments, the retinal dysfunction is a result of a tumor, a degenerative optic disease, or a congenital optical disease.

In some embodiments, the retinal dysfunction is a result of an ocular neuropathy. In some embodiments, the optic neuropathy is glaucoma, traumatic optic neuropathy, degenerative optic neuropathy, ischemic optic neuropathy, optic neuropathy from multiple sclerosis, or radiation optic neuropathy, or retinopathy.

In some embodiments, the retinal dysfunction is the result of multifocal choroiditis, birdshot chorioretinopathy, collagen vascular diseases affecting the posterior segment of the eye, Wegener's granulomatosis, peripheral uveitis, intermediate uveitis, chronic central serous chorioretinopathy, myopic choroidal neovascular membranes, myopic choroidal neovascular membranes scars, Behcet syndrome, a masquerade syndrome, ocular syphilis, ocular tuberculosis, viral-related chorioretinitis (ARN) syndrome, HIV-related uveitis, progressive outer retinal necrosis syndrome, sympathetic ophthalmia, a white dot syndrome, presumed ocular histoplasmosis syndrome, acute macular neuroretinopathy, diffuse unilateral subacute neuroretinitis, ophthalmomyiasis, serpiginous choroidopathy, panuveitis, birdshot retinochoroidopathy, uveitis associated with juvenile rheumatoid arthritis, uveitis associated with Kawasaki syndrome, uveitis associated with multiple sclerosis, uveitis associated with sarcoidosis, uveitis associated with toxocariasis, uveitis associated with toxoplasmosis, uveitis associated with systemic lupus erythematosus, uveitis associated with polyarteritis nodosa, uveitis associated with Vogt-Koyanagi-Harada, or uveitis associated with a HLA-B27 seropositive spondylopathy syndrome.

In some embodiments, the retinal dysfunction is the result of optic atrophy, ischernic optic neuropathy, diabetes induced optic atrophy, optic nerve hypoplasia, morning glory syndrome, Graves ophthalmopathy, optic neuritis, cytomegalovirus neuritis, arteritic optic neuropathy, compressive neuropathy, diabetic neuropathy, giant cell arteritis, infiltrative neuropathy, nutriotional, ischemic neuropathy, retrobulbar optic neuritis, retrobulbar ischemic neuropathy, toxic neuropathy, or traumatic neuropathy.

In some embodiments, the retinal dysfunction is the result of an optic nerve disease associated with syphilis, Lyme disease, toxoplasmosis, cat scratch disease, systemic lupus erythematosus, paraneoplastic syndrome, multiple sclerosis, or autoimmune disease.

In some embodiments, the retinal dysfunction is the result of age-related macular degeneration, early onset macular degeneration, Usher Syndrome, retinitis pigmentosa, choroideremia, cone dystrophy, cone-rod dystrophy, rod-cone dystrophy, Leber's congenital amaurosis, congenital stationary night blindness, Sticklers Syndrome, colobomas, vitreoretinal dysplasia, achromatopsia, or optic nerve hypoplasia.

In some embodiments, the inflammatory condition is multifocal choroiditis, birdshot chorioretinopathy, collagen vascular diseases affecting the posterior segment of the eye, Wegener's granulomatosis, peripheral uveitis, intermediate uveitis, chronic central serous chorioretinopathy, myopic choroidal neovascular membranes, myopic choroidal neovascular membranes scars, Behcet syndrome, a masquerade syndrome, ocular syphilis, ocular tuberculosis, viral-related chorioretinitis (ARN) syndrome, HIV-related uveitis, progressive outer retinal necrosis syndrome, sympathetic ophthalmia, a white dot syndrome, presumed ocular histoplasmosis syndrome, acute macular neuroretinopathy, diffuse unilateral subacute neuroretinitis, ophthalmomyiasis, serpiginous choroidopathy, panuveitis, or birdshot retinochoroidopathy.

In some embodiments, the inflammatory condition is uveitis associated with a disorder selected from the group consisting of juvenile rheumatoid arthritis, Kawasaki syndrome, multiple sclerosis, sarcoidosis, toxocariasis, toxoplasmosis, systemic lupus erythematosus, polyarteritis nodosa, Vogt-Koyanagi-Harada (VKH), or a HLA-B27 seropositive spondylopathy syndrome.

In some embodiments, the infection is cytomegalovirus retinitis, herpes type retinitis, Ebstein-Barr virus retinitis, toxoplasmosis, rubella, or pox virus.

In some embodiments, the optic nerve disease is optic atrophy, ischemic optic neuropathy, diabetes induced optic atrophy, optic nerve hypoplasia, morning glory syndrome, Graves ophthalmopathy, optic neuritis, cytomegalovirus neuritis, arteritic optic neuropathy, compressive neuropathy, diabetic neuropathy, giant cell arteritis, infiltrative neuropathy, nutriotional, ischemic neuropathy, retrobulbar optic neuritis, retrobulbar ischemic neuropathy, toxic neuropathy, or traumatic neuropathy.

In some embodiments, the optic nerve disease results from a cause selected from the group consisting of syphilis, Lyme disease, toxoplasmosis, cat scratch disease, systemic lupus erythematosus, paraneoplastic syndrome, multiple sclerosis, and autoimmune disease.

In some embodiments, the degenerative optic disease is the result of age-related macular degeneration, early onset macular degeneration, Usher Syndrome, retinitis pigmentosa, cone-road dystrophy, or choroideremia.

In some embodiments, the congenital optic disease is Leber's congenital amaurosis, congenital stationary night blindness, or optic nerve hypoplasia.

In some embodiments, the tumor is retinoblastoma or ocular melanoma.

In some embodiments, the dystrophic eye is the result of glaucoma.

In using the stored retinal cells to treat retinal dysfunction, one can, in conjunction with introducing the retinal cells into a recipient's eye, administer a substance that stimulates differentiation of the neuroretina-derived stem cells in the stored retinal cells into photoreceptors cells or other retinal cell types (e.g., bipolar cells, ganglion cells, horizontal cells, amacrine cells, Mueller cells). When stored retinal cells are introduced to treat a neural dysfunction of the eye, one can also utilize a substance (or combination of substances) that stimulates differentiation of the neuroretina-derived stem cells into neurons; astrocytes, or oligodendrocytes.

Kits

Also encompassed by the present invention are kits for isolating, storing and retrieving retinal cells. The kit comprises a protease, a retinal tissue digestion solution, and a retinal cell storage medium. In certain embodiments, the kit may further include a retinal cell culture medium. In certain other embodiment, the kit may further include a sterile container and a harvesting solution for harvesting retinal tissue. The harvesting solution allows the survival of the retinal tissue until later dissociation of cells from the tissue.

The harvesting solution may be any solution suitable for preserving ocular tissue. The harvesting solution may be a commercially available solution, or may be separately prepared from a serum-free tissue culture medium. Any serum-free tissue culture medium suitable for preserving ocular tissue may be used in the kits of the invention.

In some embodiments, the harvesting solution is a solution suitable for preserving corneal tissue. In some embodiments, the harvesting solution is Optisol.

In some embodiments, the harvesting solution is X-VIVO serum-free medium.

In some embodiments, the harvesting comprises an antibiotic component. As used herein, the term "antibiotic component" refers to a single antibiotic or a combination of two or more antibiotics. In some embodiments, the antibiotic combination comprises penicillin, streptomycin, or gentamicin, or a combination thereof. In some embodiments, the antibiotic component comprises penicillin and streptomycin. In some embodiments, the antibiotic component comprises penicillin and gentamicin. In some embodiments, the harvesting solution comprises X-VIVO serum-free medium and an antibiotic component comprising penicillin, streptomycin, or gentamicin or a combination thereof.

In some embodiments, the harvesting solution comprises three times the normal dosage of antibiotics. In some embodiments, the harvesting solution comprises 300 IU/ml of a combination of penicillin and streptomycin, such as that available from Gibco, Invitrogen. In some embodiments, the harvesting solution comprises 300 IU/ml of penicillin and 150 µg/ml of gentamicin. As used herein, the abbreviation "IU/ml" refers to international units of the antibiotic per ml of harvesting solution.

In some embodiments, the kit allows the survival of the tissue for up to about 7 days. In some embodiments, the kit allows the survival of the tissue for up to about 4 days. In some embodiments, the kit allows the survival of the tissue for up to about 2 days. As used herein, the term "survival" indicates that the condition of the tissue is such that retinal cells can still be isolated from the tissue.

Any sterile container can be used with the kits of the invention, including sterile vials and ampoules. In some embodiments, the sterile container comprises two or more collection vessels. In some embodiments, the two or more collection vessels are separate sterile compartments within one container, allowing the preservation of different samples of extra-ocular tissue in each collection vessel with its own supply of harvesting solution.

Certain features of the invention which are, for clarity, described herein in the context of separate embodiments, can also be provided in combination in a single embodiment. Conversely, various features of the invention which are, for brevity, described in the context of a single embodiment, can also be provided separately or in any suitable subcombination.

The present invention is further illustrated by the following examples which should not be construed as limiting. The contents of all references, patents and published patent applications cited throughout this application, as well as the Figures and Tables, are incorporated herein by reference.

Example 1: Isolation, Storage and Retrieval of Monkey Retina CFT, T, S

Isolation

Fresh monkey eyeballs were obtained from Yerkes National Primate Research Center, Atlanta, Ga. A piece of retina tissue (5 mm×5 mm) was removed from the fovea area, transferred to a 15 ml conical tube with 7 ml of retinal tissue digestion solution containing: 114 mM NaCl, 25 mM $NaHCO_3$, 1 mM sodium pyruvate, 3 mM KCl, 0.5 mM $NaH_2PO_4$, 0.5 mM $CaCl_2$, 0.02 mM phenol red. In 7 ml solution, add 3 mg cysteine HCl, 20 mg glucose, 10-14 units/ml of papain. Solution is then bubbled with 5% $CO_2$ and 95% $O_2$ until the pH is 7.2-7.3. Tissue is incubated with enzyme solution at room temperature for 30-40 minutes. After incubation, the retinal tissue digestion solution was carefully removed by aspiration. The digested retina tissue was rinsed twice with a retinal cell suspension medium containing: 139 mM NaCl, 2 mM HEPES, 1 mM sodium pyruvate, 0.5 mM $MgCl_2$, 0.5 mM $MgSO_4$, 0.5 mM $NaH_2PO_4$, 1.8 mM $CaCl_2$, 3 mM KCl, 1 mM $NaHCO_3$, 0.1 mM Choline Cl, 0.02 mM Phenol red, 15 mM glucose, with 1 N NaOH added to adjust to pH 7.2-7.3, and triturated gently in 6-14 ml of retinal cell storage medium using a 5 ml glass serological pipet to form a cell suspension containing mostly single cells.

Storage

FBS and DMSO were added to the retinal cell suspension to a final concentration of 10% (v/v) each. The cell suspension was mixed gently with FBS and DMSO, and 1 ml was aliquoted into cyroprotective vials at a cell density of $10^4$-$10^6$. The cyroprotective vials were bathed in isopropyl alcohol and placed in the −80° C. freezer, in order to cool the vials at a rate of approximately 1° C. per minute. After cooling in isopropyl alcohol, the vials were placed in a −80° C. freezer overnight. The frozen vials were then placed in a liquid nitrogen freezer in designated boxes.

Retrieval

A vial of frozen retinal cells was thawed quickly in a 37° C. water bath. The thawed cells (1 ml) were mixed gently with 10 ml warm (e.g., 37° C.) retinal cell culture medium: 139 mM NaCl, 2 mM HEPES, 1 mM sodium pyruvate, 0.5 mM $MgCl_2$, 0.5 mM $MgSO_4$, 0.5 mM $NaH_2PO_4$, 1.8 mM $CaCl_2$, 3 mM KCl, 1 mM $NaHCO_3$, 0.1 mM Choline Cl, 0.02 mM Phenol red, 15 mM glucose, add 1 N NaOH to adjust pH 7.2-7.3 and spun at 100×g for 3 min. The supernatant was removed and the cell pellet was gently resuspended in 1-2 ml retinal cell culture medium. A few drops of the suspended retinal cells were plated in a coated cell culture dish that was coated with an antibody, 9B5, that labeled living retinal cells. The cells were allowed to settle down for a few minute, then covered with more retinal cell culture medium, and incubated in the incubator at 37° C. with 5% $CO_2$.

Figure 2:
FIG. 2 is a picture of a retinal cone cell recovered from frozen cell suspension.
Figure 3:
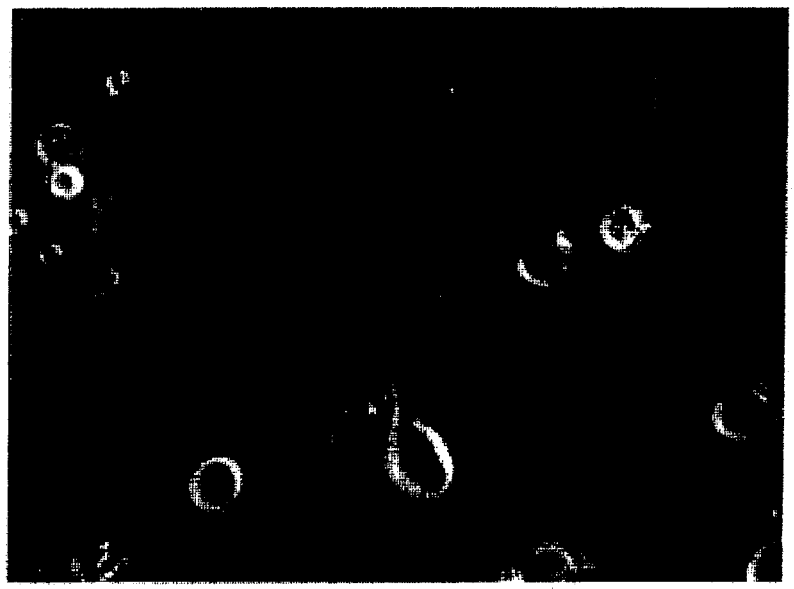
FIG. 3 is a picture of a freshly isolated retinal cone cell.

Example 2: Patch Clamp Analysis of Freshly Isolated and Frozen/Thawed Retinal Cone Cells Freshly isolated monkey retinal cone cells and retinal cone cells recovered from frozen retinal cells (stored for at least 6 months and at −170° C.) were subjected to patch clamp analysis. As shown in FIGS. 2 and 3, the retinal cone cell recovered from the frozen cell suspension (FIG. 2) is morphologically indistinguishable from the freshly isolated retinal cone cell (FIG. 3).

Figure 4:
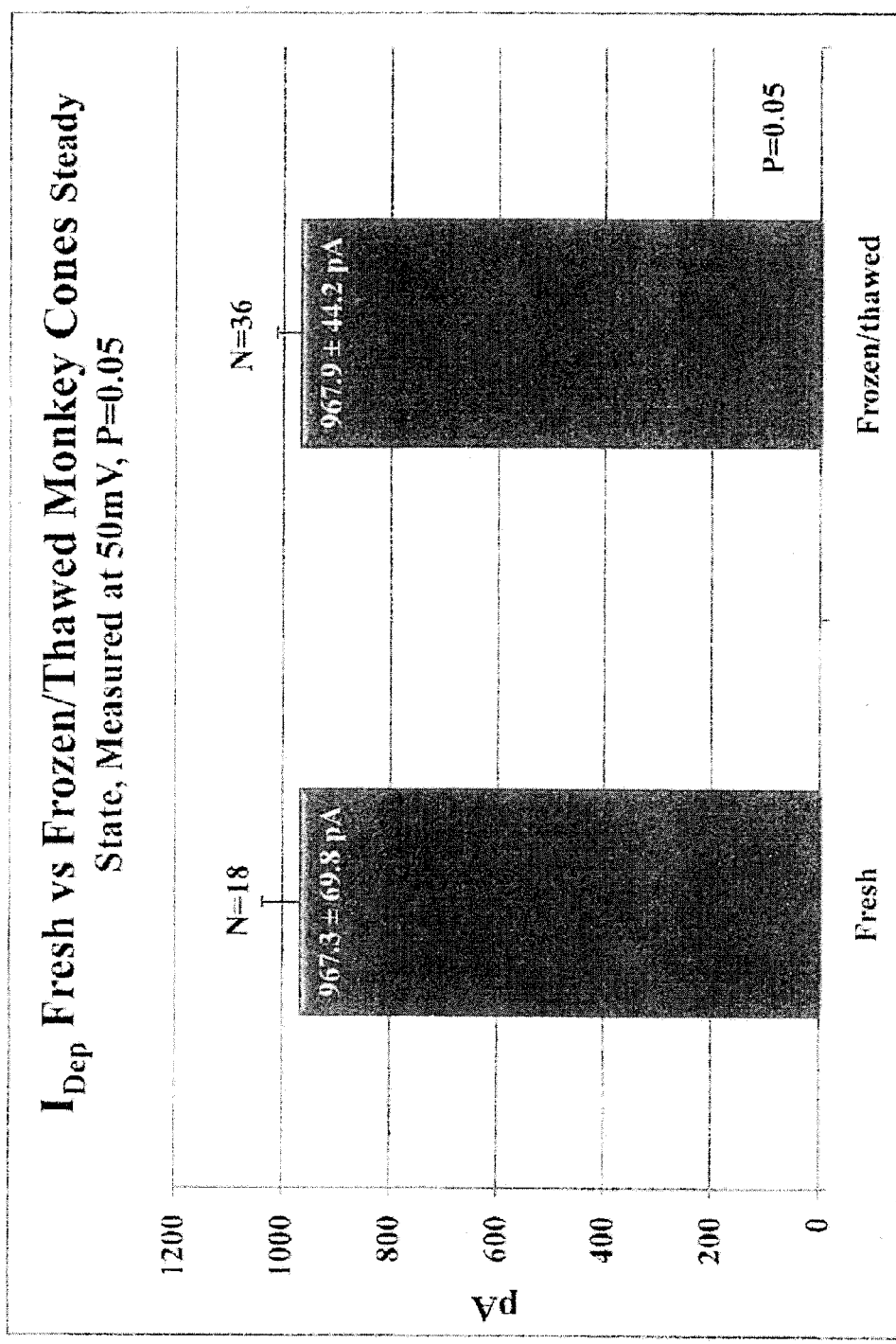
FIG. 4 is a diagram showing the average $I_{Dep}$ value measured in freshly isolated retinal cone cells and retinal cone cell recovered from frozen cell suspension.

Tables 1 and 2 show individual $I_{Dep}$ measurements in fresh retinal cone cells (Table 1) and recovered frozen retinal cone cells (Table 2). As shown in FIG. 4 and Table 3, there is no statistically significant difference (at p=0.05 level) in the $I_{Dep}$ measurements between the freshly isolated retinal cone cells and the cone cells recovered from the frozen stock.

Figure 5:
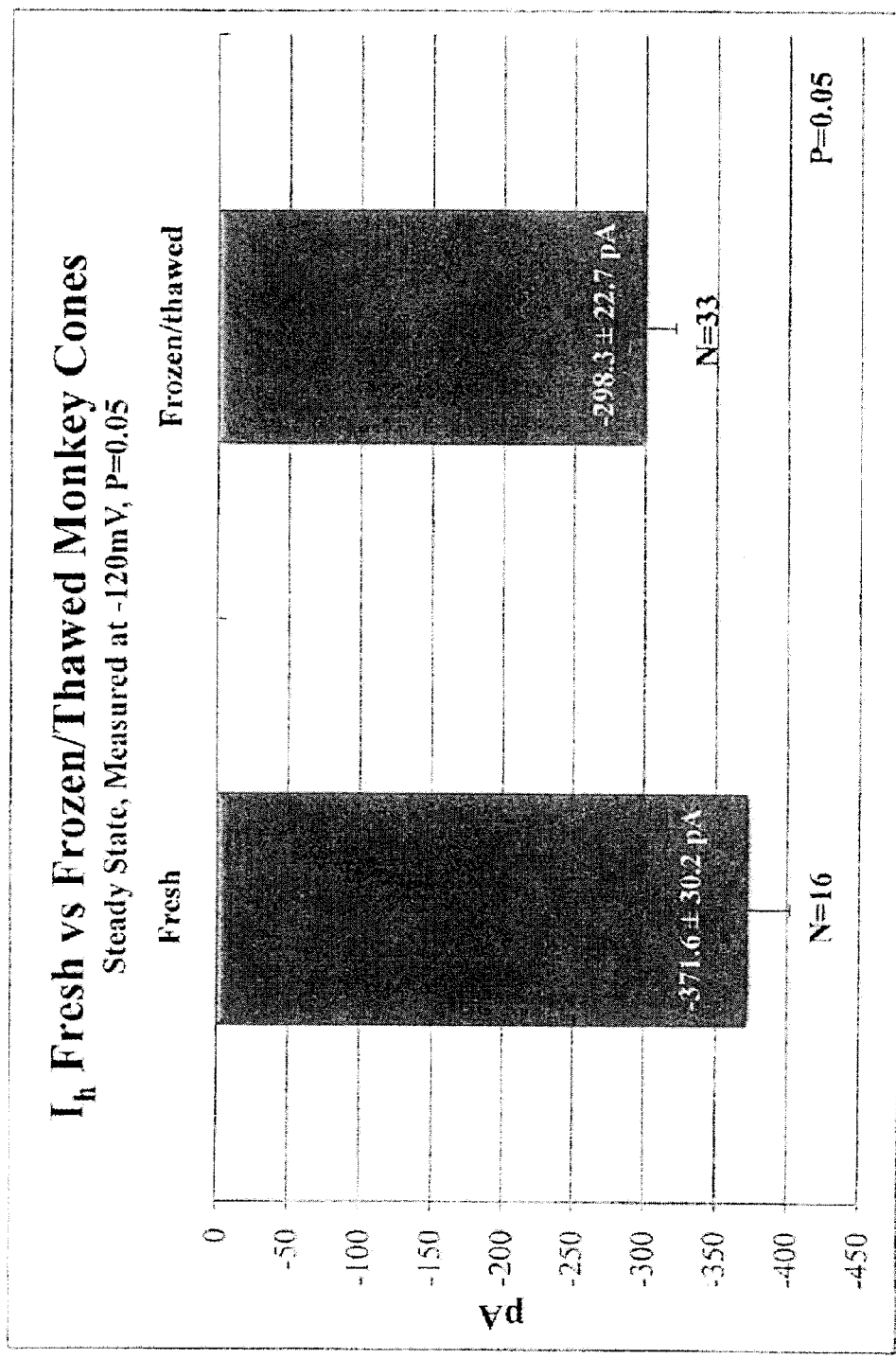
FIG. 5 is a diagram showing the average $I_h$ value measured in freshly isolated retinal cone cells and retinal cone cell recovered from frozen cell suspension.

Tables 4 and 5 show individual $I_h$ measurements in fresh retinal cone cells (Table 4) and recovered frozen retinal cone cells (Table 5). As shown in FIG. 5 and Table 6, there is no statistically significant difference (at p=0.05 level) in the $I_h$ measurements between the freshly isolated retinal cone cells and the cone cells recovered from the frozen stock.

Figure 6:
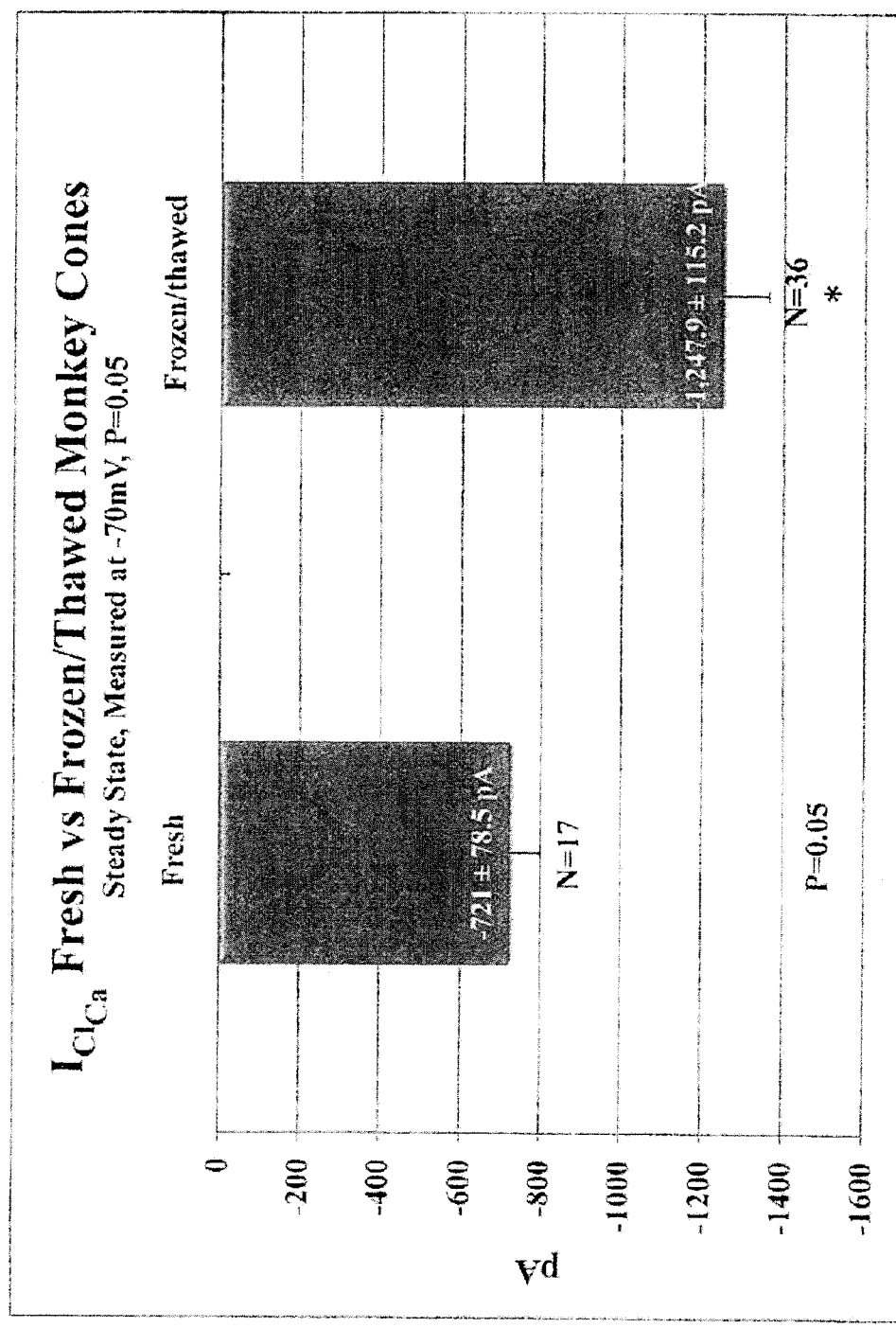
FIG. 6 is a diagram showing the average $I_{ClCa}$ value measured in freshly isolated retinal cone cells and retinal cone cell recovered from frozen cell suspension.

Tables 7 and 8 show individual $I_{ClCa}$ measurements in fresh retinal cone cells (Table 7) and recovered frozen retinal cone cells (Table 8). As shown in FIG. 6 and Table 9, there is a statistically significant difference (at p=0.05 level) in the Icica measurements between the freshly isolated retinal cone cells and the cone cells recovered from the frozen stock.

Whole-cell recording: Membrane currents were recorded in the whole-cell mode of the patch-clamp technique using an Axopatch 200 B amplifier (Axon Instruments). Dishes were mounted on a warmed (30° C.) stage of a Zeiss Axiovert 200 M microscope equipped with phase-contrast optics. Patch-clamp pipettes were pulled on a Flaming/Brown P-97 (Sutter Instruments Co. Novato, Calif.) electrode puller and had a tip diameter of about 1 μm and a resistance of approximately 6-10 MΩ. Membrane rupture was achieved by gentle suction applied to the inside of the pipette following seal formation. For most experiments, the composition of the pipette solution was as follows: 139 mM KCl, 10 mM NaCl, 10 mM HEPES, 0.05 mM EGTA, 5 mM $MgCl_2$, and 1 mM ATP. The pH was adjusted to 7.0-7.2. Data acquisition and analysis were carried out using pCLAMP software version 6.0.3 or 9.2 (Axon Instruments, Inc., Union City, Calif.).

$I_{Dep}$ is the total voltage current recorded when the membrane is depolarized from a holding potential of −70 mV. A number of different currents contribute to $I_{Dep}$ and the relative contributions differ depending on the magnitude of the voltage during the step. The individual currents are: a voltage-gated calcium current, calcium-activated chloride current, voltage-gated potassium currents. The presence of this net current indicates that the cell is alive and that the cell membrane contains active ionic conductances.

$I_h$ is a characteristic conductance found on a variety of cells including photoreceptors. It is activated by hyperpolarization and has relatively slow onset kinetics. The conductance activates at voltages negative to the holding potential of −70 mV. The presence of $I_h$ indicated that the cell has the expected properties of healthy photoreceptors.

$I_{ClCa}$ is a current that is activated when levels of calcium rise in the cell and activate a conductance that is sensitive to high levels of intracellular calcium. In our experiments shown here, calcium entry is achieved by opening voltage-gated calcium channels by depolarization for a brief amount of time. When the membrane potential is returned to the holding level of −70 mV, calcium entry is shut off and the high levels of calcium inside the cell are reduced by restorative mechanisms in the cell. The inward current seen after the voltage step is referred to as a tail current and its magnitude is controlled by the concentration of free calcium inside the cell. The size of the tail current and the time course of restoration are properties associated with healthy cells.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the components and steps in any sequence which is effective to meet the objectives there intended, unless the context specifically indicates the contrary.

TABLE 1

Fresh Monkey Cone $I_h$

| Number | Date | Trace number | Cell # | Measured voltage (mV) | Current $I_h$ (pA) | Fresh | Frozen/Thawed |
|---|---|---|---|---|---|---|---|
| 1 | Jul. 10, 2009 | 000 | 1 | −120 | −317.4 | x | |
| 2 | Aug. 8, 2008 | 005 | 1 | −120 | −372 | x | |
| 3 | Aug. 8, 2008 | 029 | 3 | −120 | −306.1 | x | |
| 4 | Aug. 8, 2008 | 039 | 4 | −120 | −363.5 | x | |
| 5 | Aug. 8, 2008 | 074 | 9 | −120 | −118 | x | |
| 6 | Aug. 8, 2008 | 078 | 10 | −120 | −322.3 | x | |
| 7 | Aug. 8, 2008 | 091 | 12 | −120 | −277.1 | x | |
| 8 | Apr. 14, 2009 | 001 | 1 | −120 | −365 | x | |
| 9 | Apr. 14, 2009 | 007 | 2 | −120 | −458 | x | |
| 10 | Apr. 15, 2009 | 002 | 1 | −120 | −419.6 | x | |
| 11 | Apr. 15, 2009 | 010 | 2 | −120 | −532 | x | |
| 12 | Apr. 15, 2009 | 024 | 5 | −120 | −535 | x | |
| 13 | Apr. 15, 2009 | 034 | 7 | −120 | −610.7 | x | |
| 14 | Apr. 16, 2009 | 013 | 4 | −120 | −375 | x | |
| 15 | Apr. 16, 2009 | 019 | 5 | −120 | −248.1 | x | |
| 16 | Apr. 16, 2009 | 042 | 9 | −120 | −326.2 | x | |

TABLE 2

Frozen/Thawed Monkey Cone $I_h$

| Number | Date | Trace number | Cell # | Measured voltage (mV) | Current $I_h$ (pA) | Fresh | Frozen/Thawed |
|---|---|---|---|---|---|---|---|
| 1 | Jun. 2, 2009 | 000 | 1 | −120 | −117.8 | | x |
| 2 | Jun. 2, 2009 | 007 | 2 | −120 | −589 | | x |
| 3 | Jun. 2, 2009 | 013 | 4 | −120 | −735 | | x |
| 4 | Jun. 3, 2009 | 001 | 1 | −120 | −324 | | x |
| 5 | Jun. 3, 2009 | 019 | 3 | −120 | −171.8 | | x |
| 6 | Jun. 3, 2009 | 046 | 4 | −120 | −122.7 | | x |
| 7 | Jun. 3, 2009 | 073 | 5 | −120 | −302.7 | | x |
| 8 | Jun. 9, 2009 | 001 | 1 | −120 | −149.2 | | x |
| 9 | Jun. 9, 2009 | 008 | 3 | −120 | −402.2 | | x |
| 10 | Jun. 9, 2009 | 023 | 4 | −120 | −265.8 | | x |
| 11 | Jun. 10, 2009 | 003 | 3 | −120 | −236.2 | | x |
| 12 | Jun. 10, 2009 | 022 | 4 | −120 | −311.9 | | x |
| 13 | Jun. 10, 2009 | 062 | 8 | −120 | −204.8 | | x |
| 14 | Jun. 23, 2009 | 002 | 2 | −120 | −499 | | x |
| 15 | Jun. 24, 2009 | 055 | 13 | −120 | −430.6 | | x |
| 16 | Jun. 24, 2009 | 066 | 14 | −120 | −447.4 | | x |
| 17 | Jun. 24, 2009 | 080 | 16 | −120 | −276.8 | | x |
| 18 | Jun. 24, 2009 | 094 | 17 | −120 | −351.9 | | x |
| 19 | Jun. 24, 2009 | 113 | 19 | −120 | −296.6 | | x |
| 20 | Jun. 25, 2009 | 006 | 3 | −120 | −294.8 | | x |
| 21 | Jun. 25, 2009 | 018 | 6 | −120 | −296.3 | | x |
| 22 | Jun. 25, 2009 | 025 | 8 | −120 | −218.2 | | x |
| 23 | Jun. 25, 2009 | 031 | 9 | −120 | −150 | | x |
| 24 | Jun. 25, 2009 | 038 | 10 | −120 | −283.2 | | x |
| 25 | Jun. 25, 2009 | 045 | 12 | −120 | −286.3 | | x |

TABLE 2-continued

Frozen/Thawed Monkey Cone $I_h$

| Number | Date | Trace number | Cell # | Measured voltage (mV) | Current $I_h$ (pA) | Fresh | Frozen/Thawed |
|---|---|---|---|---|---|---|---|
| 26 | Jun. 25, 2009 | 051 | 14 | −120 | −237.1 | | x |
| 27 | Jun. 25, 2009 | 057 | 15 | −120 | −265.2 | | x |
| 28 | Jun. 25, 2009 | 067 | 17 | −120 | −339.4 | | x |
| 29 | Jun. 25, 2009 | 074 | 16 | −120 | −259.4 | | x |
| 30 | Jun. 25, 2009 | 104 | 25 | −120 | −298.5 | | x |
| 31 | Jun. 25, 2009 | 110 | 26 | −120 | −295.4 | | x |
| 32 | Jun. 25, 2009 | 115 | 27 | −120 | −170.9 | | x |
| 33 | Jun. 25, 2009 | 121 | 29 | −120 | −213.6 | | x |

TABLE 3

Means Comparison using Tukey Test

| Dataset | Mean Difference between Confidence Intervals | | | Significant at 0.05 | |
|---|---|---|---|---|---|
| Data8_A | 967.31667 | Means | Lower Limit | Upper Limit | Level |
| Data8_B | 967.89167 | −0.575 | −160.37786 | 159.22786 | No |

Power Analysis

| Alpha | Total Sample Size | Power |
|---|---|---|
| 0.05 | 54 | 0.05001 (actual) |

At the 0.05 level, the population means are not significantly different.

TABLE 4

Fresh Monkey Cone $I_{Dep}$

| Number | Date | Trace number | Cell # | Measured voltage (mV) | Current $I_{Dep}$ (pA) | Fresh | Frozen/Thawed |
|---|---|---|---|---|---|---|---|
| 1 | Jul. 10, 2009 | 003 | 1 | 50 | 833 | x | |
| 2 | Aug. 8, 2008 | 002 | 1 | 50 | 945.1 | x | |
| 3 | Aug. 8, 2008 | 024 | 3 | 50 | 1111.3 | x | |
| 4 | Aug. 8, 2008 | 038 | 4 | 50 | 671.7 | x | |
| 5 | Aug. 8, 2008 | 069 | 8 | 50 | 574.6 | x | |
| 6 | Aug. 8, 2008 | 073 | 9 | 50 | 548.4 | x | |
| 7 | Aug. 8, 2008 | 077 | 10 | 50 | 805.8 | x | |
| 8 | Aug. 8, 2008 | 090 | 12 | 50 | 809.3 | x | |
| 9 | Aug. 8, 2008 | 096 | 13 | 50 | 1029.1 | x | |
| 10 | Apr. 14, 2009 | 002 | 1 | 50 | 1658.9 | x | |
| 11 | Apr. 14, 2009 | 008 | 2 | 50 | 1327.8 | x | |
| 12 | Apr. 15, 2009 | 003 | 1 | 50 | 1004 | x | |
| 13 | Apr. 15, 2009 | 011 | 2 | 50 | 542.3 | x | |
| 14 | Apr. 15, 2009 | 025 | 5 | 50 | 1345.8 | x | |
| 15 | Apr. 15, 2009 | 035 | 7 | 50 | 1021.7 | x | |
| 16 | Apr. 16, 2009 | 014 | 4 | 50 | 957.6 | x | |
| 17 | Apr. 16, 2009 | 020 | 5 | 50 | 1064.1 | x | |
| 18 | Apr. 16, 2009 | 044 | | | 1161.2 | x | |

TABLE 5

Frozen/Thawed Monkey Cone $I_{Dep}$

| Number | Date | Trace number | Cell # | Measured voltage (mV) | Current $I_{Dep}$ (pA) | Fresh | Frozen/Thawed |
|---|---|---|---|---|---|---|---|
| 1 | Jun. 2, 2009 | 002 | 1 | 50 | 377.8 | | x |
| 2 | Jun. 2, 2009 | 008 | 2 | 50 | 1233.2 | | x |
| 3 | Jun. 2, 2009 | 012 | 4 | 50 | 1496 | | x |
| 4 | Jun. 3, 2009 | 003 | 1 | 50 | 808.7 | | x |
| 5 | Jun. 3, 2009 | 018 | 3 | 50 | 1182.3 | | x |
| 6 | Jun. 3, 2009 | 045 | 4 | 50 | 937.2 | | x |
| 7 | Jun. 3, 2009 | 074 | 5 | 50 | 947.9 | | x |
| 8 | Jun. 9, 2009 | 000 | 1 | 50 | 1091.3 | | x |
| 9 | Jun. 9, 2009 | 009 | 3 | 50 | 853 | | x |
| 10 | Jun. 9, 2009 | 022 | 4 | 50 | 850.8 | | x |
| 11 | Jun. 10, 2009 | 004 | 3 | 50 | 1134.3 | | x |
| 12 | Jun. 10, 2009 | 023 | 4 | 50 | 760.8 | | x |
| 13 | Jun. 10, 2009 | 056 | 8 | 50 | 1022.3 | | x |
| 14 | Jun. 19, 2009 | 009 | 3 | 50 | 1448.7 | | x |
| 15 | Jun. 19, 2009 | 014 | 4 | 50 | 1640.6 | | x |
| 16 | Jun. 19, 2009 | 022 | 6 | 50 | 1287.5 | | x |
| 17 | Jun. 23, 2009 | 001 | 2 | 50 | 1046.1 | | x |
| 18 | Jun. 24, 2009 | 053 | 13 | 50 | 1056.2 | | x |
| 19 | Jun. 24, 2009 | 065 | 14 | 50 | 1084.6 | | x |
| 20 | Jun. 24, 2009 | 081 | 16 | 50 | 527.6 | | x |
| 21 | Jun. 24, 2009 | 091 | 17 | 50 | 1048.3 | | x |
| 22 | Jun. 24, 2009 | 112 | 19 | 50 | 754.7 | | x |
| 23 | Jun. 25, 2009 | 005 | 3 | 50 | 939.3 | | x |
| 24 | Jun. 25, 2009 | 016 | 6 | 50 | 1063.5 | | x |
| 25 | Jun. 25, 2009 | 023 | 8 | 50 | 995.8 | | x |
| 26 | Jun. 25, 2009 | 030 | 9 | 50 | 1004.6 | | x |
| 27 | Jun. 25, 2009 | 036 | 10 | 50 | 1142 | | x |
| 28 | Jun. 25, 2009 | 043 | 12 | 50 | 859.7 | | x |
| 29 | Jun. 25, 2009 | 049 | 14 | 50 | 783.7 | | x |
| 30 | Jun. 25, 2009 | 056 | 15 | 50 | 580.1 | | x |
| 31 | Jun. 25, 2009 | 066 | 17 | 50 | 802.6 | | x |
| 32 | Jun. 25, 2009 | 072 | 18 | 50 | 1059.3 | | x |
| 33 | Jun. 25, 2009 | 102 | 25 | 50 | 799 | | x |
| 34 | Jun. 25, 2009 | 108 | 26 | 50 | 606 | | x |
| 35 | Jun. 25, 2009 | 113 | 27 | 50 | 939.3 | | x |
| 36 | Jun. 25, 2009 | 119 | 29 | 50 | 679.3 | | x |

TABLE 6

Means Comparison using Tukey Test

| Dataset | Mean Difference between Confidence Intervals | | | Significant at 0.05 | |
|---|---|---|---|---|---|
| Data5_A | −371.625 | Means | Lower Limit | Upper Limit | Level |
| Data5_B | −298.29394 | −73.33106 | −151.543 | 4.88088 | No |

Power Analysis

| Alpha | Total Sample Size | Power |
|---|---|---|
| 0.05 | 49 | 0.45535 (actual) |

At the 0.05 level, the population means are not significantly different.

TABLE 7

Fresh Monkey Cone $I_{Cl(Ca)}$

| Number | Date | Trace number | Cell # | Measured voltage (mV) | Current $I_{Cl(Ca)}$ (pA) | Fresh | Frozen/Thawed |
|---|---|---|---|---|---|---|---|
| 1 | Jul. 10, 2009 | 001 | 1 | −70 | −650 | x | |
| 2 | Aug. 8, 2008 | 000 | 1 | −70 | −1036.6 | x | |
| 3 | Aug. 8, 2008 | 023 | 3 | −70 | −690 | x | |
| 4 | Aug. 8, 2008 | 040 | 4 | −70 | −471 | x | |
| 5 | Aug. 8, 2008 | 067 | 8 | −70 | −425 | x | |
| 6 | Aug. 8, 2008 | 075 | 10 | −70 | −444.3 | x | |

TABLE 7-continued

Fresh Monkey Cone $I_{Cl(Ca)}$

| Number | Date | Trace number | Cell # | Measured voltage (mV) | Current $I_{ClCa}$ (pA) | Fresh | Frozen/Thawed |
|---|---|---|---|---|---|---|---|
| 7 | Aug. 8, 2008 | 088 | 12 | −70 | −313.9 | x | |
| 8 | Aug. 8, 2008 | 096 | 13 | −70 | −786.9 | x | |
| 9 | Apr. 14, 2009 | 000 | 1 | −70 | −1588.7 | x | |
| 10 | Apr. 14, 2009 | 006 | 2 | −70 | −1146.5 | x | |
| 11 | Apr. 15, 2009 | 000 | 1 | −70 | −412.3 | x | |
| 12 | Apr. 15, 2009 | 009 | 2 | −70 | −813.6 | x | |
| 13 | Apr. 15, 2009 | 023 | 5 | −70 | −931.4 | x | |
| 14 | Apr. 15, 2009 | 033 | 7 | −70 | −491.6 | x | |
| 15 | Apr. 16, 2009 | 012 | 4 | −70 | −656.4 | x | |
| 16 | Apr. 16, 2009 | 018 | 5 | −70 | −835 | x | |
| 17 | Apr. 16, 2009 | 041 | 9 | −70 | −564.9 | x | |

TABLE 8

Frozen/Thawed Monkey Cone $I_{Cl(Ca)}$

| Number | Date | Trace number | Cell # | Measured voltage (mV) | Current $I_{ClCa}$ (pA) | Fresh | Frozen/Thawed |
|---|---|---|---|---|---|---|---|
| 1 | Jun. 2, 2009 | 001 | 1 | | −1192 | | x |
| 2 | Jun. 2, 2009 | 005 | 2 | | −2883.2 | | x |
| 3 | Jun. 2, 2009 | 014 | 4 | | −2671.5 | | x |
| 4 | Jun. 3, 2009 | 002 | 1 | | −606.7 | | x |
| 5 | Jun. 3, 2009 | 020 | 3 | | −639.6 | | x |
| 6 | Jun. 3, 2009 | 047 | 4 | | −494.4 | | x |
| 7 | Jun. 3, 2009 | 075 | 5 | | −1001 | | x |
| 8 | Jun. 9, 2009 | 002 | 1 | | −1418.5 | | x |
| 9 | Jun. 9, 2009 | 010 | 3 | | −612.8 | | x |
| 10 | Jun. 9, 2009 | 021 | 4 | | −378.4 | | x |
| 11 | Jun. 10, 2009 | 005 | 3 | | −1359.9 | | x |
| 12 | Jun. 10, 2009 | 024 | 4 | | −620.7 | | x |
| 13 | Jun. 10, 2009 | 063 | 8 | | −412 | | x |
| 14 | Jun. 19, 2009 | 007 | 3 | | −1511.2 | | x |
| 15 | Jun. 19, 2009 | 015 | 4 | | −1946.4 | | x |
| 16 | Jun. 19, 2009 | 021 | 6 | | −1185.9 | | x |
| 17 | Jun. 23, 2009 | 003 | 2 | | −1099.1 | | x |
| 18 | Jun. 24, 2009 | 054 | 13 | | −2035.8 | | x |
| 19 | Jun. 24, 2009 | 068 | 14 | | −2345.3 | | x |
| 20 | Jun. 24, 2009 | 079 | 16 | | −620.7 | | x |
| 21 | Jun. 24, 2009 | 090 | 17 | | −1835.3 | | x |
| 22 | Jun. 24, 2009 | 114 | 19 | | −1717.2 | | x |
| 23 | Jun. 25, 2009 | 003 | 3 | | −1870.1 | | x |
| 24 | Jun. 25, 2009 | 015 | 6 | | −1443.5 | | x |
| 25 | Jun. 25, 2009 | 021 | 8 | | −2568.1 | | x |
| 26 | Jun. 25, 2009 | 028 | 9 | | −743.2 | | x |
| 27 | Jun. 25, 2009 | 035 | 10 | | −1517.6 | | x |
| 28 | Jun. 25, 2009 | 042 | 12 | | −1361.7 | | x |
| 29 | Jun. 25, 2009 | 048 | 14 | | −281 | | x |
| 30 | Jun. 25, 2009 | 061 | 15 | | −390 | | x |
| 31 | Jun. 25, 2009 | 068 | 17 | | −803.8 | | x |
| 32 | Jun. 25, 2009 | 071 | 18 | | −1661.4 | | x |
| 33 | Jun. 25, 2009 | 105 | 25 | | −892.8 | | x |
| 34 | Jun. 25, 2009 | 107 | 26 | | −949.6 | | x |
| 35 | Jun. 25, 2009 | 112 | 27 | | −865.5 | | x |
| 36 | Jun. 25, 2009 | 118 | 29 | | −991.8 | | x |

TABLE 9

Means Comparison using Tukey Test

| Dataset | Mean Difference between Confidence Intervals | Simultaneous | | Significant at 0.05 Level |
|---|---|---|---|---|
| Data2_A | −721.06471 | Means | Lower Limit | Upper Limit | |
| Data2_B | −1247.99167 | 526.92696 | 171.80147 | 882.05245 | Yes |

TABLE 9-continued

Power Analysis

| Alpha | Total Sample Size | Power |
|---|---|---|
| 0.05 | 53 | 0.83206 (actual) |

At the 0.05 level, the population means are significantly different.

What is claimed is:

1. A method for the isolation and storage of mature retinal cone cells, comprising:
    (a) incubating freshly isolated retinal tissue with a retinal tissue digestion solution comprising a protease and $CaCl_2$;
    (b) removing said retinal tissue digestion solution to yield an enzyme-treated retinal tissue;
    (c) triturating said enzyme-treated retinal tissue in a retinal cell suspension medium to form a retinal cell suspension;
    (d) adding fetal bovine serum (FBS) and dimethyl sulfoxide (DMSO) to said retinal cell suspension comprising retinal cone cells;
    (e) freezing and storing said retinal cell suspension comprising FBS and DMSO in liquid nitrogen;
    (f) thawing said retinal cell suspension;
    (g) washing and culturing said thawed retinal cells with a retinal cell culture medium comprising Choline Cl; and isolating mature retinal cone cells recovered from said frozen retinal cell suspension,
    wherein said isolated mature retinal cone cells are capable of maintaining $I_{Dep}$ and $I_h$ levels after being frozen for at least 6 months at −170° C. that are not statistically different from $I_{Dep}$ and $I_h$ levels of freshly isolated retinal cone cells not subjected to freezing and thawing as measured by patch clamp analysis.

2. The method of claim 1, further comprising: dissecting said isolated retinal tissue into small fragments.

3. The method of claim 1, wherein said protease is selected from the group consisting of trypsin, chymotrypsin, pepsin, papain, elastase A and mixtures thereof.

4. The method of claim 3, wherein said protease is papain.

5. The method of claim 3, wherein said tissue digestion solution further comprises a collagenase.

6. The method of claim 3, wherein said tissue digestion solution further comprises an enzyme activator.

7. The method of claim 6, wherein said enzyme activator is cysteine.

8. The method of claim 1, wherein said tissue digestion solution comprises NaCl, $NaHCO_3$, sodium pyruvate, KCl, and $NaH_2PO_4$.

9. The method of claim 1, wherein said tissue digestion solution comprises 114 mM NaCl, 25 mM $NaHCO_3$, 1 mM sodium pyruvate, 3 mM KCl, 0.5 mM $NaH_2PO_4$, 0.5 mM $CaCl_2$, and 0.02 mM Phenol red.

10. The method of claim 1, wherein said tissue digestion solution has a pH of 7.2-7.3.

11. The method of claim 1, wherein said freshly isolated retinal tissue is incubated with a retinal tissue digestion solution comprising a protease at a temperature between about 18° C. and 42° C. for about 15-90 min.

12. The method of claim 1, wherein said freshly isolated retinal tissue is incubated with a retinal tissue digestion solution comprising a protease at room temperature for about 30-40 min.

13. The method of claim 1, wherein said retinal cell culture medium comprises a growth factor selected from the group consisting of human epidermal growth factor, human fibroblast growth factor-2 and platelet-derived growth factor.

14. The method of claim 13, wherein the retinal cell culture medium further comprises insulin, h-transferrin, putrascine, selenite and glutamine.

15. The method of claim 1, wherein said isolated mature retinal cone cells have an $I_{ClCa}$ level that is statistically lower than the $I_{ClCa}$ level of freshly isolated retinal cone cells as measured by patch clamp analysis, after being frozen for at least 6 months at −170° C.

16. The method of claim 1, wherein the retinal cell culture medium comprises preconditioned culture medium prepared by culturing Muller glial cells in a culture medium suitable for cone survival.

17. The method of claim 1, wherein said retinal cell culture medium comprises platelet-derived growth factor.

18. The method of claim 1, further comprising the step of dissecting freshly isolated retinal tissue into small fragments in cold $CO_2$-independent medium, prior to incubation with the retinal tissue digestion solution comprising the protease and CaCl2.

* * * * *